US011191957B2

(12) United States Patent
    Kobayashi

(10) Patent No.: US 11,191,957 B2
(45) Date of Patent: Dec. 7, 2021

(54) LIVING BODY STIMULATION DEVICE

(71) Applicant: TECHNO LINK CO., LTD., Niigata (JP)

(72) Inventor: Tatsuyuki Kobayashi, Niigata (JP)

(73) Assignee: TECHNO LINK CO., LTD., Niigata (JP)

( * ) Notice: Subject to any disclaimer, the term of this patent is extended or adjusted under 35 U.S.C. 154(b) by 20 days.

(21) Appl. No.: 16/621,128

(22) PCT Filed: Oct. 10, 2018

(86) PCT No.: PCT/JP2018/037753
§ 371 (c)(1),
(2) Date: Dec. 10, 2019

(87) PCT Pub. No.: WO2019/130715
PCT Pub. Date: Jul. 4, 2019

(65) Prior Publication Data
US 2020/0114147 A1    Apr. 16, 2020

(30) Foreign Application Priority Data

Dec. 25, 2017   (JP) .............................. JP2017-247986

(51) Int. Cl.
    *A61N 1/36*    (2006.01)
    *A61N 1/08*    (2006.01)
    *A61N 1/40*    (2006.01)

(52) U.S. Cl.
    CPC ................. *A61N 1/36* (2013.01); *A61N 1/08* (2013.01); *A61N 1/40* (2013.01)

(58) Field of Classification Search
    CPC ... A61N 1/36; A61N 1/08; A61N 1/40; A61N 1/36034
    See application file for complete search history.

(56) References Cited

U.S. PATENT DOCUMENTS 6,526,319 B2    2/2003  Kobayashi
2005/0146308 A1* 7/2005  Quazi ................. H02M 7/2176
                                                        322/28
(Continued)

FOREIGN PATENT DOCUMENTS

JP         3503135 B2    3/2004
JP       2005224387 A    8/2005
(Continued)

OTHER PUBLICATIONS

International Search Report issued in corresponding International Application No. PCT/JP2018/037753 dated Nov. 6, 2018 (3 pages).
(Continued)

*Primary Examiner* — Catherine M Voorhees
(74) *Attorney, Agent, or Firm* — Osha Bergman Watanabe & Burton LLP

(57) ABSTRACT

A living body stimulation device includes an outputting unit that outputs a stimulation signal to a living body. The stimulation signal is a signal in which a positive pulse group and a negative pulse group appear alternately at predetermined intervals. The positive pulse group is constituted by a plurality of pulses whose potential rises toward the plus-side. The negative pulse group is constituted by a plurality of pulses whose potential falls toward the minus-side.

8 Claims, 12 Drawing Sheets

(56) References Cited

U.S. PATENT DOCUMENTS

| | | | |
|---|---|---|---|
| 2009/0216293 A1 | 8/2009 | Sasaki et al. | |
| 2012/0232611 A1* | 9/2012 | Sasaki ................ | A61N 1/36034 607/42 |
| 2015/0335888 A1* | 11/2015 | Demers .............. | A61N 1/36025 607/45 |
| 2017/0224990 A1* | 8/2017 | Goldwasser ......... | A61N 1/0456 |

FOREIGN PATENT DOCUMENTS

| | | |
|---|---|---|
| JP | 2006-526980 A | 11/2006 |
| JP | 2011188926 A | 9/2011 |
| WO | 2006/054359 A1 | 5/2006 |

OTHER PUBLICATIONS

Written Opinion issued in corresponding International Application No. PCT/JP2018/037753 dated Nov. 6, 2018 (4 pages).
Extended European Search Report issued in corresponding European Patent Application No. 18897100.6, dated Jan. 13, 2021 (7 pages).

* cited by examiner

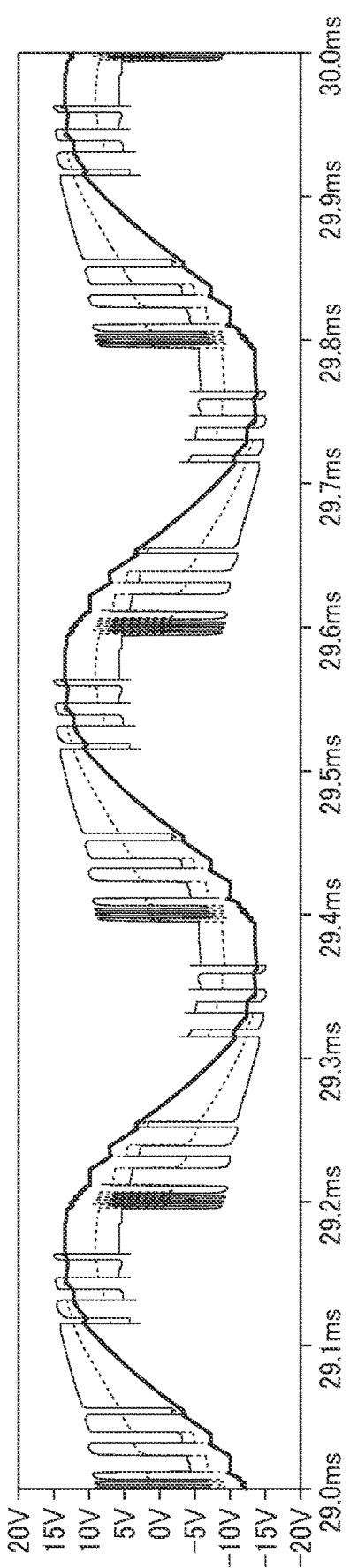
FIG. 6A (2500 HZ: THREE DISCHARGE PULSES)
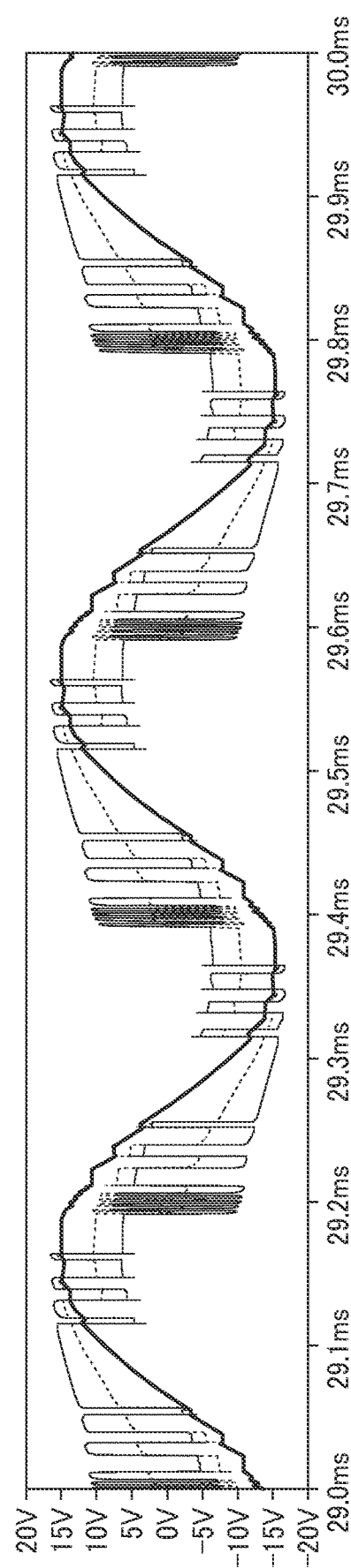
FIG. 6B (2500 HZ: FOUR DISCHARGE PULSES)

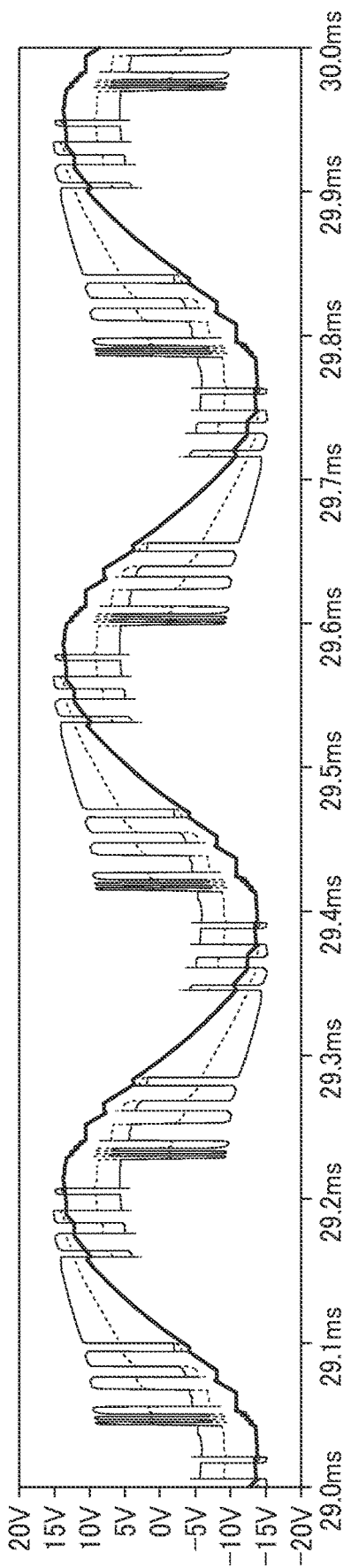
FIG. 7A (2700 HZ: TWO DISCHARGE PULSES)
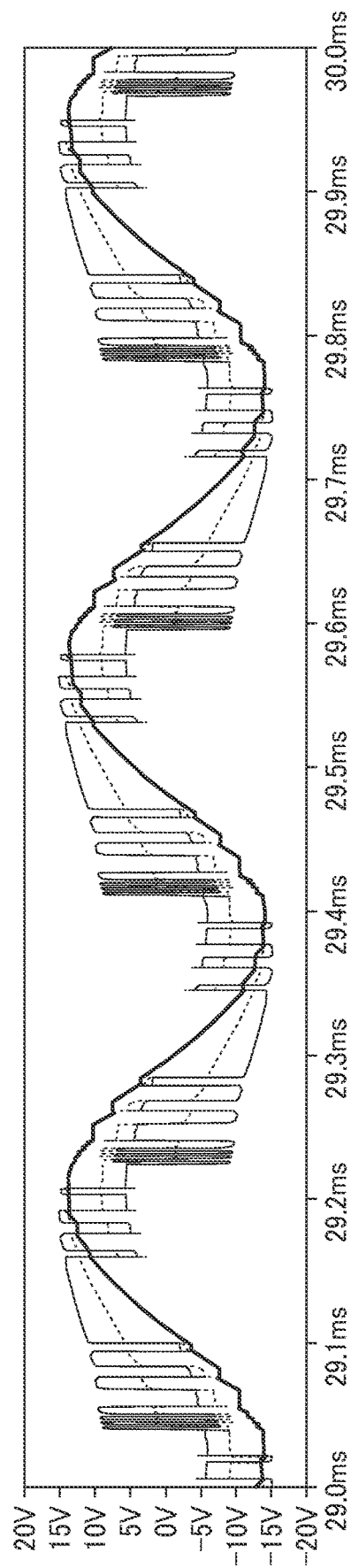
FIG. 7B (2700 HZ: THREE DISCHARGE PULSES)

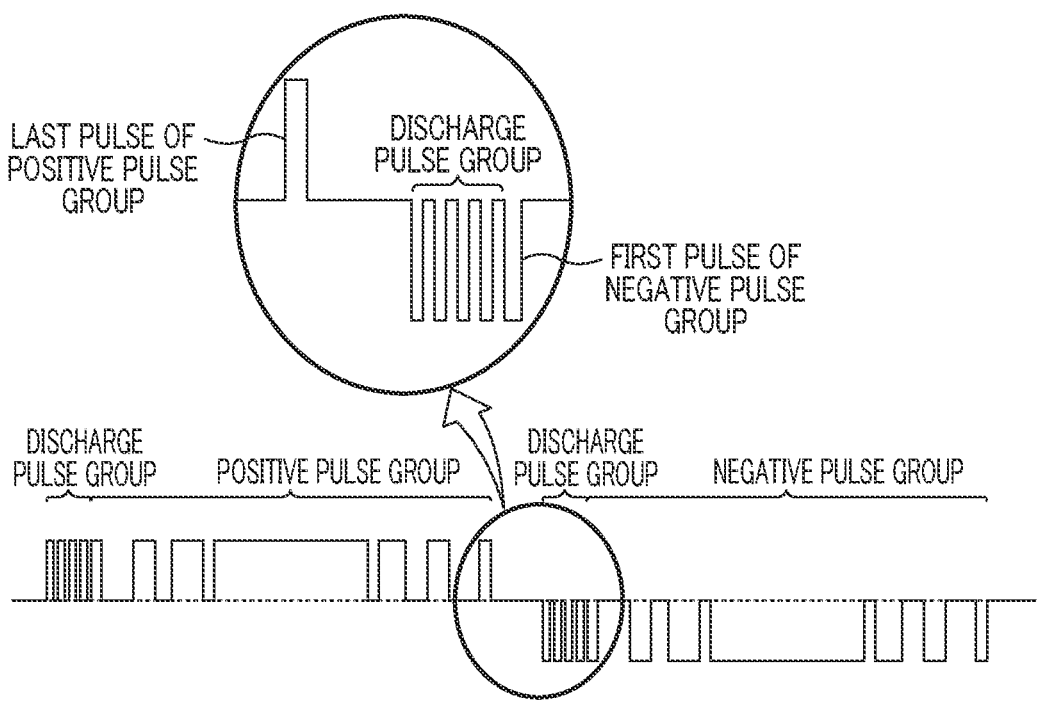
FIG. 8A (REFERENCE EXAMPLE: HALT TERM BETWEEN DISCHARGE PULSES IS CONSTANT)
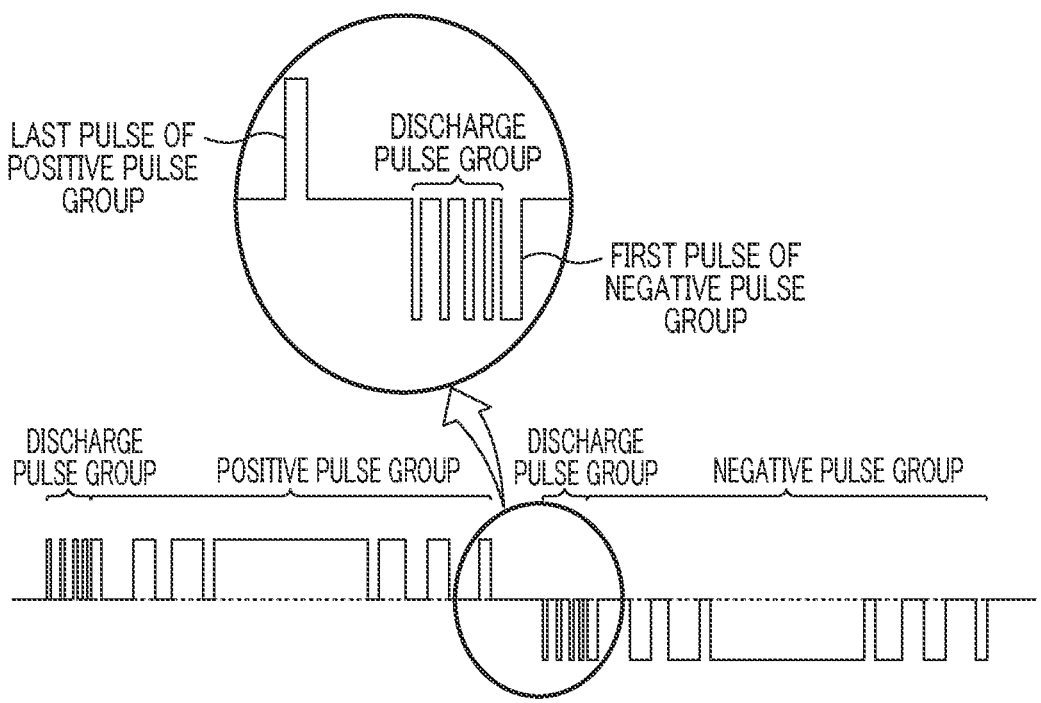
FIG. 8B (REFERENCE EXAMPLE: HALT TERM BETWEEN DISCHARGE PULSES GRADUALLY DECREASES)

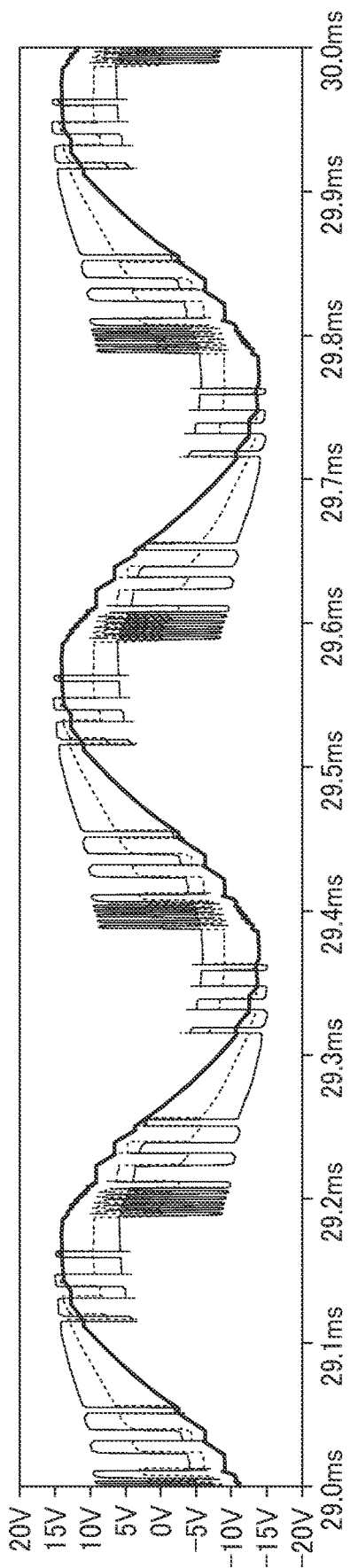
FIG. 9A (2500 HZ: HALT TERM BETWEEN DISCHARGE PULSES IS CONSTANT)
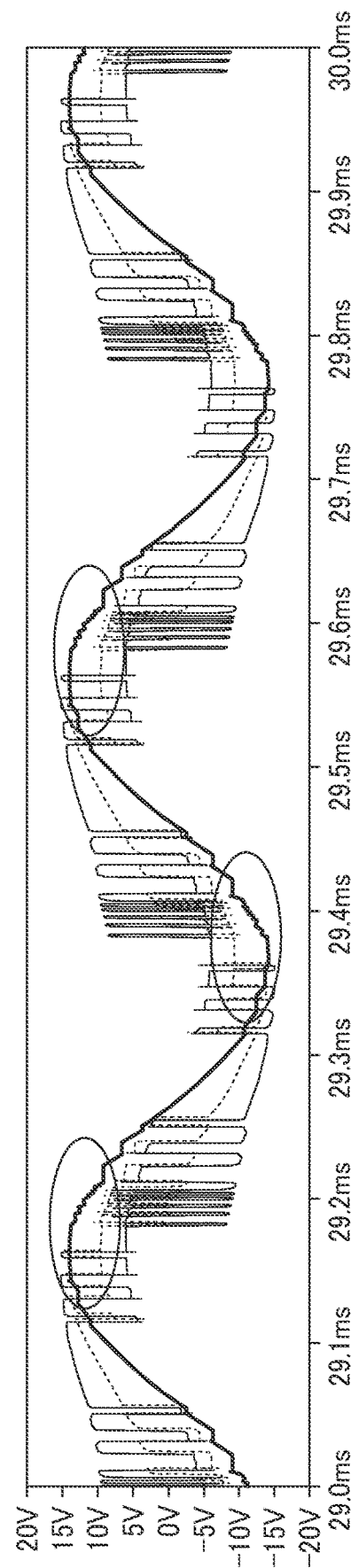
FIG. 9B (2500 HZ: HALT TERM BETWEEN DISCHARGE PULSES GRADUALLY DECREASES)

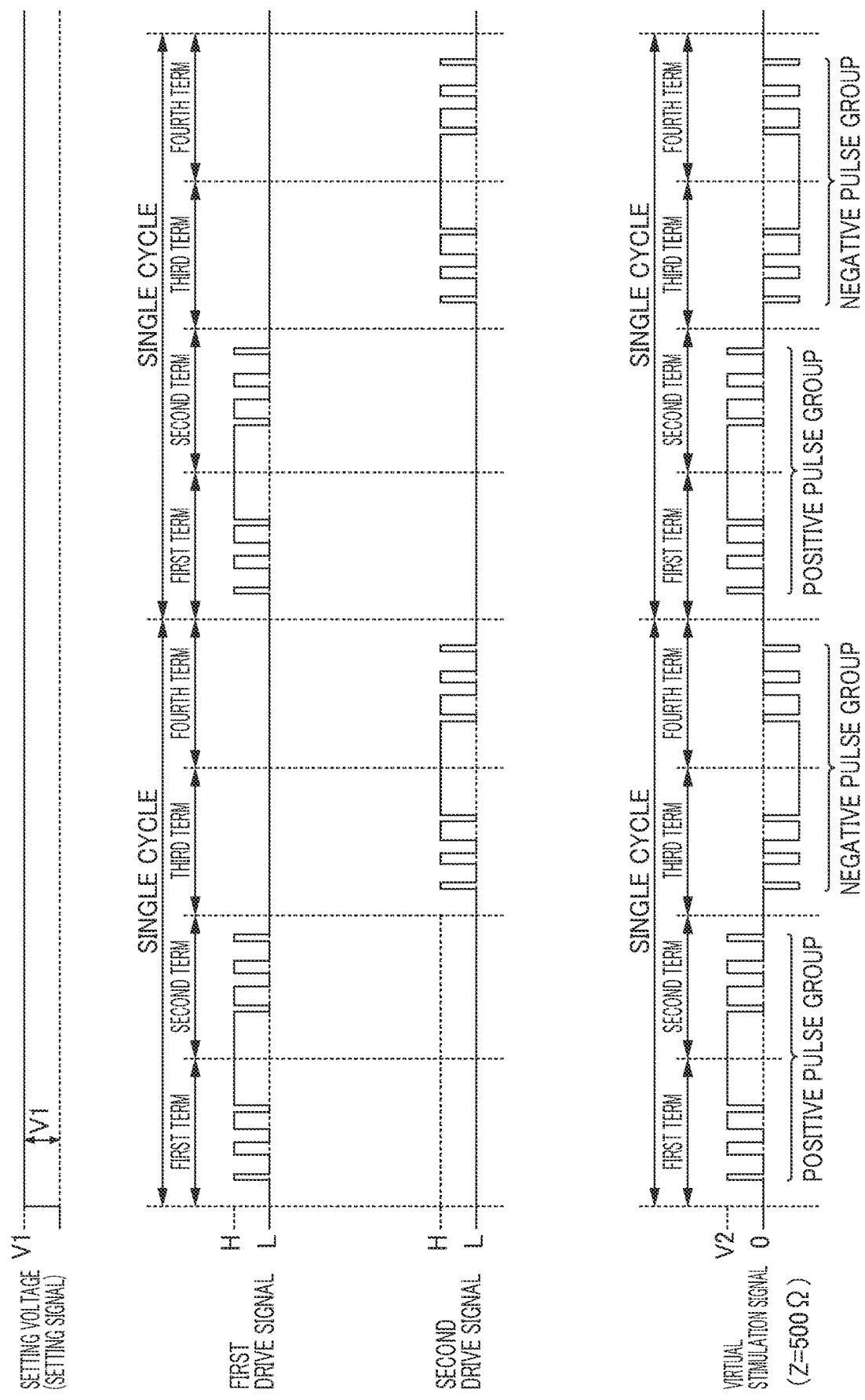
FIG. 10 COMPARATIVE EXAMPLE

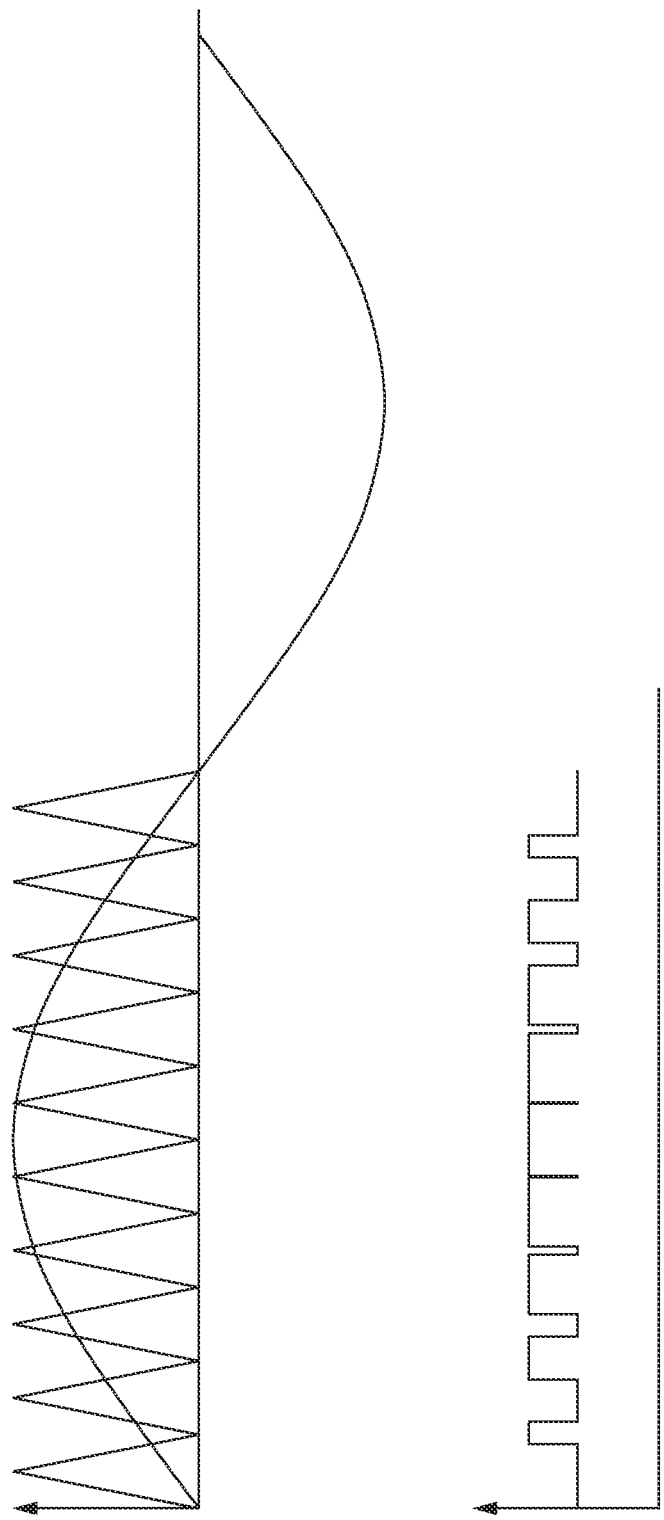

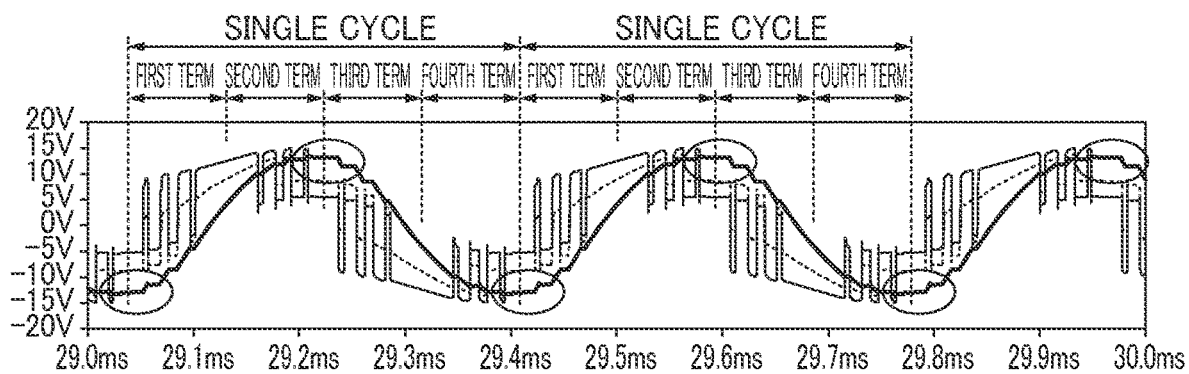
FIG. 12A (COMPARATIVE EXAMPLE)
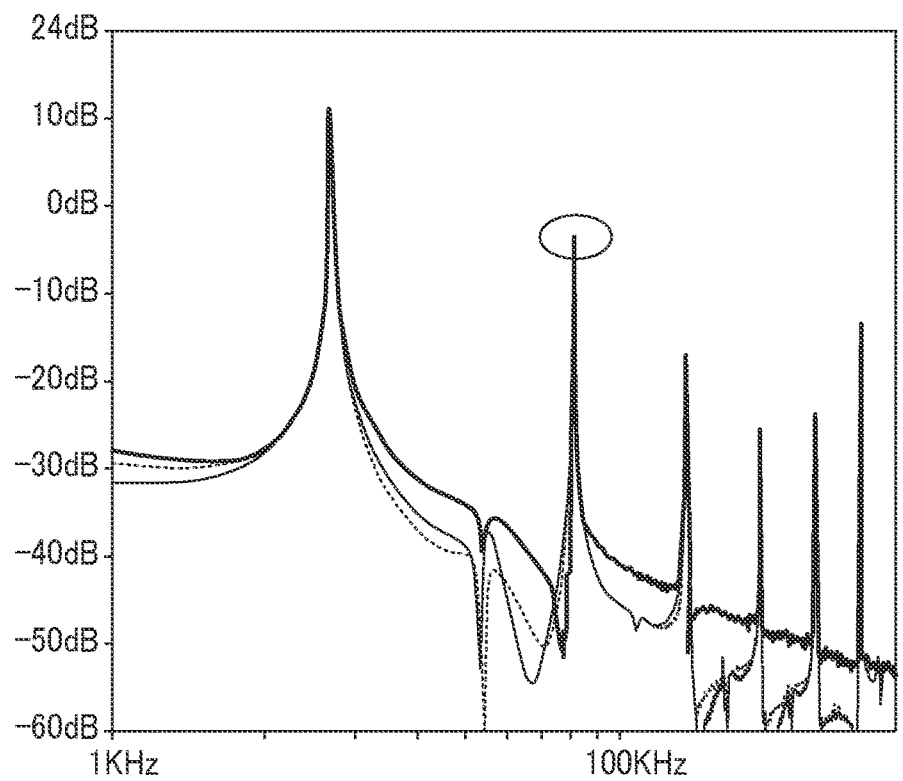
FIG. 12B (COMPARATIVE EXAMPLE)

LIVING BODY STIMULATION DEVICE

TECHNICAL FIELD

The present invention relates to a living body stimulation device.

BACKGROUND ART

Living body stimulation devices for passing a current (stimulation signal) through a living body from a conductor element (outputting unit) having a built-in electrode are known in the art. Such living body stimulation devices provide stimulation to a living body by passing a stimulation signal therethrough, to thereby stimulate the nerves or cause muscle contraction/relaxation. For example, Patent Literature 1 discloses a living body stimulation apparatus that stimulates a living body by outputting a stimulation signal from a conductor element connected to a secondary winding of an output transformer.

CITATION LIST

Patent Literature

Patent Literature 1: Japanese Patent No. 3503135

SUMMARY

Technical Problem

The living body stimulation apparatus disclosed in Patent Literature 1 focuses on the fact that a living body has capacitive properties like a capacitor, and employs the action of the living body's capacitive properties to distort pulse groups and thereby form pseudo-sine waves to thus apply a soft feeling of stimulation. The inventor of the present application, however, has found that, in conventional art, the waveform in the vicinity of the peaks (the highest potential point or the lowest potential point) of the sine wave is distorted by later-described reactive properties specific to living bodies. It is desirable to reduce such distortions in waveform in order to obtain an even softer feeling of stimulation.

An objective of the present invention is to suppress distortions in the waveform of a pseudo-sine wave.

Solution to Problem

A main aspect of the invention to achieve the above objective is a living body stimulation device including an outputting unit that outputs a stimulation signal to a living body. The stimulation signal is a signal in which a positive pulse group and a negative pulse group appear alternately at predetermined intervals, the positive pulse group being constituted by a plurality of pulses whose potential rises toward the plus-side, the negative pulse group being constituted by a plurality of pulses whose potential falls toward the minus-side. When a single period of the stimulation signal is divided into four terms consisting of a first term, a second term, a third term, and a fourth term: the positive pulse group appears in the first term and the second term, wherein, in the first term, the pulse width gradually widens, and in the second term, the pulse width gradually narrows in a manner that change-over-time thereof is reverse of the change-over-time of the pulse width in the first term; and the negative pulse group appears in the third term and the fourth term, wherein, in the third term, the pulse width gradually widens, and in the fourth term, the pulse width gradually narrows in a manner that change-over-time thereof is reverse of the change-over-time of the pulse width in the third term. The stimulation signal includes: a discharge pulse that is provided immediately before the positive pulse group and whose potential rises toward the plus-side; and a discharge pulse that is provided immediately before the negative pulse group and whose potential falls toward the minus-side.

Other features of the present invention are disclosed in the following description and accompanying drawings.

Advantageous Effects of Invention

The present invention is capable of suppressing distortions in the waveform of a pseudo-sine wave.

BRIEF DESCRIPTION OF DRAWINGS

FIGS. 6A and 6B are graphs for when a 2500-Hz stimulation signal is outputted from the outputting units 31 in a state connected with body resistance Z. FIG. 6A is a graph for when a discharge pulse group is constituted by three discharge pulses, and FIG. 6B is a graph for when a discharge pulse group is constituted by four discharge pulses.

FIGS. 7A and 7B are graphs for when a 2700-Hz stimulation signal is outputted from the outputting units 31 in a state connected with body resistance Z. FIG. 7A is a graph for when a discharge pulse group is constituted by two discharge pulses, and FIG. 7B is a graph for when a discharge pulse group is constituted by three discharge pulses.

FIG. 8A is a diagram illustrating a virtual stimulation signal according to a reference example. FIG. 8B is a diagram illustrating a third embodiment.

FIGS. 9A and 9B are graphs for when a stimulation signal is outputted from the outputting units 31 in a state connected with body resistance Z. In FIG. 9A, the halt term between discharge pulses is constant. In FIG. 9B, the halt term between discharge pulses gradually decreases.

FIG. 10 is a diagram illustrating various types of signals according to a comparative example.

FIG. 11 is a diagram illustrating each of the pulses in a pulse group of a first drive signal (and a second drive signal).

FIG. 12A is a graph for when a stimulation signal of the comparative example is outputted from the outputting units 31 in a state connected with body resistance Z. FIG. 12B is a graph illustrating a FFT analysis result of FIG. 12A.

DESCRIPTION OF EMBODIMENTS

Figure 1:
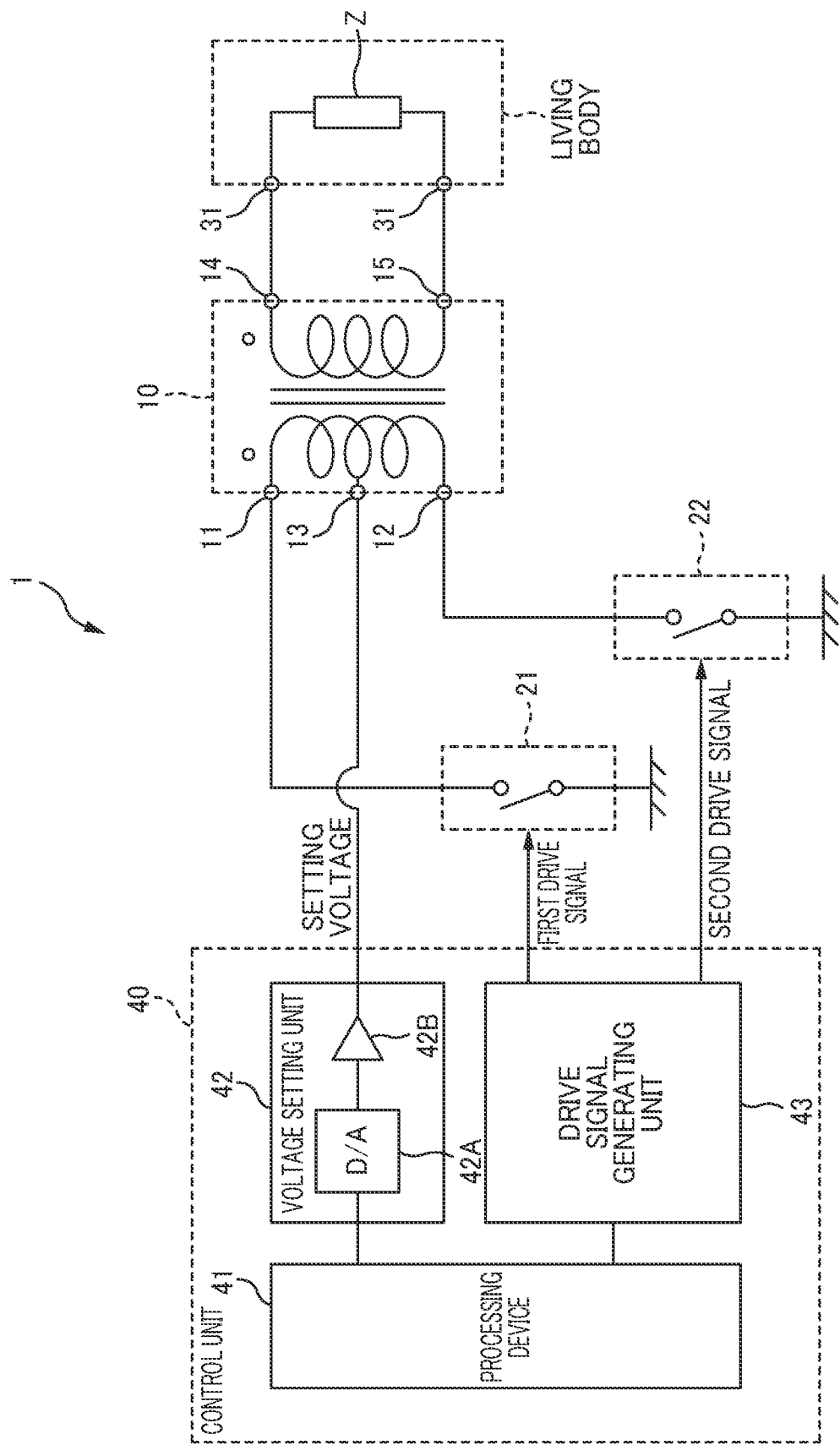
FIG. 1 is a diagram illustrating a configuration of a living body stimulation device 1 according to an embodiment.

At least the following features are disclosed in the following description and accompanying drawings.

Disclosed is a living body stimulation device including an outputting unit that outputs a stimulation signal to a living body. The stimulation signal is a signal in which a positive pulse group and a negative pulse group appear alternately at predetermined intervals, the positive pulse group being constituted by a plurality of pulses whose potential rises toward the plus-side, the negative pulse group being constituted by a plurality of pulses whose potential falls toward the minus-side. When a single period of the stimulation signal is divided into four terms consisting of a first term, a second term, a third term, and a fourth term: the positive pulse group appears in the first term and the second term, wherein, in the first term, the pulse width gradually widens, and in the second term, the pulse width gradually narrows in a manner that change-over-time thereof is reverse of the change-over-time of the pulse width in the first term; and the negative pulse group appears in the third term and the fourth term, wherein, in the third term, the pulse width gradually widens, and in the fourth term, the pulse width gradually narrows in a manner that change-over-time thereof is reverse of the change-over-time of the pulse width in the third term. The stimulation signal includes: a discharge pulse that is provided immediately before the positive pulse group and whose potential rises toward the plus-side; and a discharge pulse that is provided immediately before the negative pulse group and whose potential falls toward the minus-side. With this living body stimulation device, distortion in the waveform of a pseudo-sine wave can be suppressed.

Preferably, when the pulse width of the discharge pulse is defined as A and the pulse width of a first pulse in the positive pulse group or the negative pulse group is defined as B, A is set to less than or equal to B. In this way, stimulation to a living body by the discharge pulse can be suppressed.

Preferably, the stimulation signal includes a discharge pulse group constituted by a plurality of the discharge pulses. In this way, discharging of redundant charge can be promoted.

Preferably, a frequency of the plurality of discharge pulses constituting the discharge pulse group is higher than a frequency of the plurality of pulses constituting the positive pulse group or the negative pulse group. In this way, stimulation to a living body by the discharge pulse group can be suppressed.

Preferably, the number of discharge pulses constituting the discharge pulse group is changeable depending on the frequency of the stimulation signal. In this way, distortion in the waveform of a pseudo-sine wave can be suppressed.

Preferably, the number of discharge pulses constituting the discharge pulse group is changeable depending on a halt term between the positive pulse group and the negative pulse group. In this way, distortion in the waveform of a pseudo-sine wave can be suppressed.

Preferably, the discharge pulse group is constituted by at least three discharge pulses, and a halt term between the discharge pulses is set so as to gradually shorten. In this way, distortion in the waveform of a pseudo-sine wave can be suppressed.

Also disclosed is a living body stimulation device that outputs a stimulation signal to a living body, the living body stimulation device including: an output transformer; a first switch configured to pass, through a primary side of the output transformer, a current in a predetermined direction; a second switch configured to pass, through the primary side of the output transformer, a current in an opposite direction from the predetermined direction; a control unit that generates a first drive signal that drives the first switch, and a second drive signal that drives the second switch; and an outputting unit that outputs the stimulation signal on a secondary side of the output transformer. The first drive signal and the second drive signal are each a signal in which a pulse group constituted by a plurality of pulses appears at predetermined intervals. When a single period is divided into four terms consisting of a first term, a second term, a third term, and a fourth term: the pulse group of the first drive signal appears in the first term and the second term, wherein, in the first term, the pulse width gradually widens, and in the second term, the pulse width gradually narrows in a manner that change-over-time thereof is reverse of the change-over-time of the pulse width in the first term; and the pulse group of the second drive signal appears in the third term and the fourth term, wherein, in the third term, the pulse width gradually widens, and in the fourth term, the pulse width gradually narrows in a manner that change-over-time thereof is reverse of the change-over-time of the pulse width in the third term. The first drive signal and the second drive signal each include a discharge pulse immediately before the pulse group. With this living body stimulation device, distortion in the waveform of a pseudo-sine wave can be suppressed.

First Embodiment

Basic Configuration:

FIG. 1 is a diagram illustrating a configuration of a living body stimulation device 1 according to the present embodiment. In the figure, the reference sign Z indicates the resistance of a living body (e.g., the human body). An equivalent circuit of the body resistance Z will be described further below (cf. FIG. 2B).

The living body stimulation device 1 is a device that applies stimulation to a living body by a stimulation signal outputted from outputting units 31. Passing a current by the stimulation signal through a living body stimulates the nerves and causes muscle contraction/relaxation, thereby applying stimulation to the body. In general, the higher the frequency of the stimulation signal, the smaller the body impedance and the weaker the sense of muscle stimulation. For example, at high frequencies of 100 kHz or higher, the stimulation signal causes almost no muscle stimulation. In contrast, the lower the frequency of the stimulation signal, the greater the body impedance and the stronger the feeling of stimulation. At low frequencies which offer a feeling of stimulation, the stimulation is softer when the stimulation signal is a sine wave rather than a rectangular wave.

The living body stimulation device 1 includes an output transformer 10, a first switch 21, a second switch 22, outputting units 31, and a control unit 40.

The output transformer 10 is a converter (transformer) that converts signals between a primary-side winding and a secondary-side winding. The output transformer 10 converts electric energy supplied to the primary side into magnetic energy, and then re-converts the magnetic energy into electric energy on the secondary side and outputs the same as a stimulation signal.

The output transformer 10 includes a first input terminal 11, a second input terminal 12, a center tap 13, a first output terminal 14, and a second output terminal 15. The first input terminal 11, the second input terminal 12, and the center tap 13 are provided on the primary side of the output transformer 10. The first input terminal 11 is a terminal on one-end side of the primary-side winding. The second input terminal 12 is a terminal on the other-end side (the opposite side from the first input terminal) of the primary-side winding. The center tap 13 is a terminal drawn out from an intermediate point of the primary-side winding. The first output terminal 14 and the second output terminal 15 are provided on the secondary side of the output transformer 10.

The first switch 21 is a switch configured to pass, through the primary-side winding of the output transformer 10, a current in the plus direction (predetermined direction). The first switch 21 is connected to the first input terminal 11 on one-end side of the primary-side winding of the output transformer 10. The first switch 21 is a FET, for example; the drain of the FET, whose source is grounded, is connected to the first input terminal 11, and on/off (energization/non-energization) is controlled according to a signal inputted to the gate. When the first switch 21 is on, a current in the plus direction flows through the primary-side winding. When the first switch 21 is off, the current in the plus direction is interrupted.

The second switch 22 is a switch configured to pass, through the primary-side winding of the output transformer 10, a current in the minus direction (opposite direction from the predetermined direction). The second switch 22 is a switch connected to the second input terminal 12 on the other-end side (opposite side from the side where the first switch 21 is connected) of the primary-side winding of the output transformer 10. Like the first switch 21, the second switch 22 is a FET, for example; the drain of the FET, whose source is grounded, is connected to the second input terminal 12, and on/off is performed according to a signal inputted to the gate. When the second switch 22 is on, a current in the minus direction flows through the primary-side winding. When the second switch 22 is off, the current in the minus direction is interrupted.

The outputting units 31 are electrodes that output a stimulation signal to a living body. The outputting units 31 are respectively connected to the first output terminal 14 and the second output terminal 15 of the secondary-side winding of the output transformer 10. Each outputting unit 31 is built into a conductor element (e.g., an adhesive pad, a suction pad, or a metal-rod-shaped or glove-shaped conductor element) to be placed in contact with a living body, and outputs a stimulation signal to the body via the conductor element.

The control unit 40 is a section (controller) that controls the drive of the first switch 21 and the second switch 22. Stated differently, the control unit 40 controls the input to the output transformer 10 via the first switch 21 and the second switch 22. The control unit 40 also controls the voltage of the center tap 13 of the primary-side winding of the output transformer 10. By executing a program stored in a storage unit (not illustrated), the control unit 40 executes various types of processing as described further below. In this embodiment, the control unit 40 includes a processing device 41, a voltage setting unit 42, and a drive signal generating unit 43.

The processing device 41 is a processing device 41 such as a CPU or an MPU. The processing device 41 outputs, to the voltage setting unit 42, a setting signal for designating a setting voltage. Also, the processing device 41 outputs, to the drive signal generating unit 43, an instruction signal for instructing the generation of a first drive signal and a second drive signal.

The voltage setting unit 42 is a section (circuit) that sets the voltage (setting voltage) of the center tap 13 of the output transformer 10. In this embodiment, the voltage setting unit 42 includes a D/A converter 42A and an amplifier 42B. The D/A converter 42A outputs a voltage according to a signal inputted from the processing device 41. The amplifier 42B sets the voltage of the center tap 13 by amplifying the output voltage from the D/A converter 42A. When the setting signal from the processing device 41 changes, the setting voltage of the center tap 13 of the output transformer 10 is changed, and thereby the voltage of the stimulation signal is adjusted. It should be noted that the voltage setting unit 42 does not have to be configured such that the setting voltage to be outputted to the center tap 13 is variable, but may be configured so as to output a constant voltage.

The drive signal generating unit 43 is a signal generating unit (circuit) that generates a first drive signal and a second drive signal. The drive signal generating unit 43 outputs the first drive signal to the first switch 21 (more specifically, the gate of the first switch 21, which is a FET), and outputs the second drive signal to the second switch 22 (more specifically, the gate of the second switch 22, which is a FET). It should be noted that the control unit 40 may be configured such that the processing device 41 outputs the first drive signal and the second drive signal to the first switch 21 and the second switch 22, without providing the drive signal generating unit 43.

Comparative Example

A comparative example will be described first, before describing the present embodiment.

FIG. 10 is a diagram illustrating various types of signals according to a comparative example. In the figure, the horizontal axis indicates time, and the vertical axis indicates voltage. The various types of signals illustrated in the figure are, in order from above, the setting voltage, the first drive signal, the second drive signal, and a virtual stimulation signal for explanation.

The setting voltage is the voltage (potential) of the center tap 13 of the output transformer 10. In this example, the setting voltage is V1, but the control unit 40 is capable of changing the setting voltage V1, and thereby, the intensity (V2) of the stimulation signal can be adjusted.

The first drive signal is a signal (drive signal, switch control signal) for driving the first switch 21. When the first drive signal is at level H, the first switch 21 is turned on, and the setting voltage is applied to the primary-side winding between the first input terminal 11 and the center tap 13 of the output transformer 10, thereby causing a current in the plus direction (predetermined direction) to flow through the primary-side winding (energization). When the first drive signal is at level L, the first switch 21 is turned off, and the current in the plus direction is interrupted (non-energization).

The second drive signal is a signal for driving the second switch 22. When the second drive signal is at level H, the second switch 22 is turned on, and the setting voltage is applied to the primary-side winding between the second input terminal 12 and the center tap 13 of the output transformer 10, thereby causing a current in the minus direction (opposite direction from the predetermined direction) to flow through the primary-side winding. When the second drive signal is at level L, the second switch 22 is turned off, and the current in the minus direction is interrupted.

The first drive signal and the second drive signal are each a signal in which a pulse group (corresponding to the later-described sine wave pulse group) constituted by a plurality of pulses appears at predetermined intervals. The pulse group of the first drive signal and the second drive signal is constituted as a PWM signal, and each pulse constituting the pulse group is set to a pulse width adjusted to a predetermined duty cycle. The period of the pulse group is relatively long (i.e., low frequency), whereas the period of the plurality of pulses constituting the pulse group is relatively short. The pulse group of the first drive signal and the pulse group of the second drive signal occur alternately. Thus, the first switch 21 and the second switch 22 perform high-frequency switching operation alternately. Note that the energization term of the pulse group of the first drive signal does not overlap the energization term of the pulse group of the second drive signal, and when the pulse group of one drive signal is in its energization term, the other drive signal is in its halt term. Stated differently, the phase of the first drive signal and that of the second drive signal are shifted by 180 degrees from one another.

In the description below, a period of time worth a single cycle (i.e., a single period) of the first drive signal (or the second drive signal) may be divided into four equal terms, and these terms may respectively be called first to fourth terms. The first term and the second term constitute the energization term of the pulse group of the first drive signal and constitute the halt term of the second drive signal. The third term and the fourth term constitute the halt term of the first drive signal and constitute the energization term of the pulse group of the second drive signal.

In the first term (the former half of the energization term of the first drive signal), the pulse width of the plurality of pulses constituting the pulse group of the first drive signal gradually widens (the duty cycle gradually increases), and in the second term (the latter half of the energization term of the first drive signal), the pulse width gradually narrows (the duty cycle gradually decreases). Further, the pulse width in the second term changes over time in a manner that the change-over-time thereof is reverse of the change-over-time of the pulse width in the first term.

In the third term (the former half of the energization term of the second drive signal), the pulse width of the plurality of pulses constituting the pulse group of the second drive signal gradually widens, and in the fourth term (the latter half of the energization term of the second drive signal), the pulse width gradually narrows. Further, the pulse width in the fourth term changes over time in a manner that the change-over-time thereof is reverse of the change-over-time of the pulse width in the third term. The change-over-time of the pulse width of the second drive signal in the third term is the same as the change-over-time of the pulse width of the first drive signal in the first term. The change-over-time of the pulse width of the second drive signal in the fourth term is the same as the change-over-time of the pulse width of the first drive signal in the second term.

FIG. 11 is a diagram illustrating each of the pulses in a pulse group of the first drive signal (and the second drive signal).

For example, the drive signal generating unit 43 includes a comparator (not illustrated). To the comparator are inputted a sine wave signal and a triangular wave signal, as illustrated in the upper graph of FIG. 11. In this example, the period (cycle) of the sine wave signal in the figure is identical to the period (cycle) of the pulse group of the first drive signal (or the second drive signal). In this example, the frequency of the triangular wave signal is ten times that of the sine wave signal (although not limited to tenfold). When the voltage of the triangular wave signal is higher (or lower) than that of the sine wave signal, the comparator sets the voltage of the first drive signal (or the second drive signal) to level L. When the voltage of the triangular wave signal is lower (or higher) than that of the sine wave signal, the comparator sets the voltage of the first drive signal (or the second drive signal) to level H. In this way, a first drive signal as illustrated in the lower graph of FIG. 11 is outputted from the comparator. It should be noted that, although short halt terms (L-level signals) are created in the vicinity of the peak of sine wave signal, such short halt terms make almost no contribution; thus, the short halt terms are cancelled, and a wide pulse is generated. Note, however, that such short halt terms may be reproduced in the first drive signal (or the second drive signal).

In the aforementioned first drive signal, the pulse width gradually widens in the first term, and the pulse width gradually narrows in the second term. Further, the pulse width in the second term changes over time in a manner that the change-over-time thereof is reverse of the change-over-time of the pulse width in the first term.

In the example above, the configuration of the first drive signal (and the second drive signal) was described assuming that the drive signal generating unit 43 included a comparator. It should be noted, however, that the drive signal generating unit 43 does not have to include a comparator. For example, data on the change-over-time of the pulse width may be stored in advance, and the first drive signal (and the second drive signal) may be generated by sequentially generating pulses at time widths according to the data.

The virtual stimulation signal illustrated in FIG. 10 is a signal in a state where there is no distortion in waveform caused by the body's reactance characteristics. When a resistance (e.g., 500Ω) including no capacitive component nor inductive component is connected to the outputting units 31, a signal substantially matching the virtual stimulation signal will be outputted from the outputting units 31.

As illustrated in FIG. 10, in the stimulation signal, plus-side pulse groups (positive pulse groups) and minus-side pulse groups (negative pulse groups) appear alternately at predetermined intervals.

The positive pulse group is a pulse group constituted by a plurality of pulses whose potential rises toward the plus-side. The positive pulse groups are generated by the pulse groups of the first drive signal. More specifically, the positive pulse group is generated as a result of the first drive signal causing the first switch 21 to turn on/off, thereby causing a current in the plus direction (predetermined direction) to flow through the primary-side winding between the first input terminal 11 and the center tap 13 of the output transformer 10.

The negative pulse group is a pulse group constituted by a plurality of pulses whose potential falls toward the minus-side. The negative pulse groups are generated by the pulse groups of the second drive signal. More specifically, the negative pulse group is generated as a result of the second drive signal causing the second switch 22 to turn on/off, thereby causing a current in the minus direction (opposite direction from the predetermined direction) to flow through the primary-side winding between the second input terminal 12 and the center tap 13 of the output transformer 10.

In the description below, a period of time worth a single cycle (i.e., a single period) of the stimulation signal may be divided into four equal terms, and these terms may respectively be called first to fourth terms, like the first to fourth terms of the first drive signal. The positive pulse group of the stimulation signal appears in the first term and the second term, and the negative pulse group appears in the third term and the fourth term.

The virtual stimulation signal illustrated in the figure is in a state with no distortion in waveform, and the envelope of the pulse group has a low-frequency rectangular shape (rectangular pulse form). However, a living body, which is the output destination of the outputting units 31, has capacitive properties like a capacitor; the action of the body's capacitive properties causes the rectangular pulses to distort, thereby being able to form a pseudo-sine wave. This is described below.

Figure 2A:
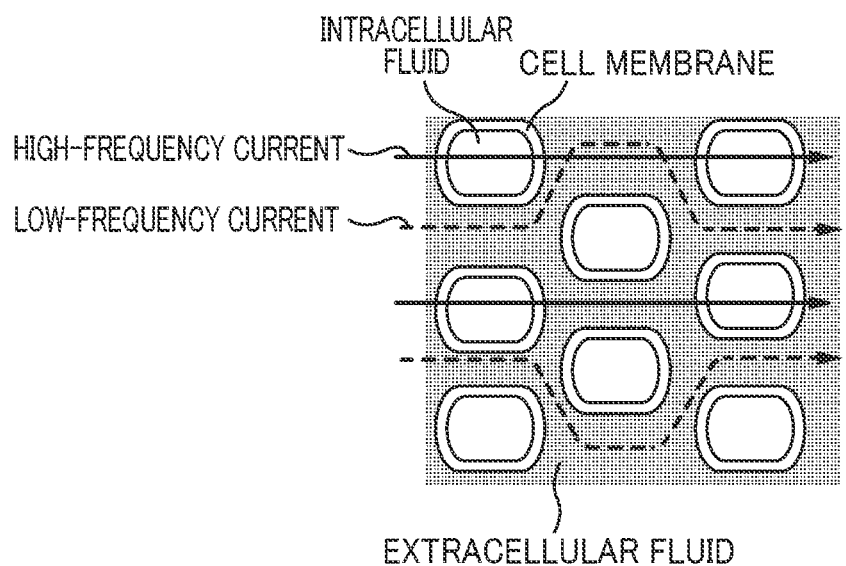
FIG. 2A is a diagram illustrating how a current flows through biological tissue.
Figure 2B:
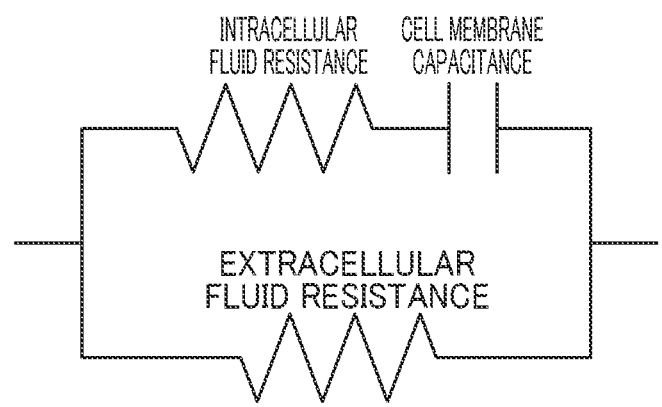
FIG. 2B is a diagram illustrating an equivalent circuit of body resistance Z.

FIG. 2A is a diagram illustrating how a current flows through biological tissue. FIG. 2B is a diagram illustrating an equivalent circuit of body resistance Z.

It is considered that a current passing through biological tissue follows different paths depending on frequency. Currents at low frequencies cannot pass through cell membranes, and thus flow through extracellular fluid outside the cells. Currents at higher frequencies are able to pass through cell membranes, and thus also flow intracellularly (through the cell membranes and intracellular fluid). As illustrated in FIG. 2B, the extracellular fluid and the intracellular fluid can be considered resistive components (resistance), whereas the cell membrane can be considered a capacitive component (reactance).

FIG. 12A is a graph (simulation result) for when a stimulation signal according to the comparative example is outputted from the outputting units 31 in a state connected with body resistance Z. The horizontal axis of the graph indicates time, and the vertical axis indicates voltage between the outputting units 31. Note that the frequency is 2700 Hz (a single cycle is around 370 μs). FIG. 12B is a graph illustrating a FFT analysis result of FIG. 12A. In this example, the capacitance of a cell membrane is 1 μF, and the extracellular fluid resistance is 2 kΩ. The thick solid line, the dotted line, and the thin solid line in the graph respectively indicate different intracellular fluid resistances, which are 1(Ω), 41(Ω), and 100(Ω), respectively. The intracellular fluid resistance close to that of a living body is 41Ω, but in order to describe the phenomenon of pseudo-sine wave distortion, the figures focus on the example in which the intracellular fluid resistance is 1Ω.

As illustrated in FIG. 12A, since the body resistance Z includes a capacitive component, the voltage of the stimulation signal (the envelope of the voltage of the stimulation signal when the intracellular fluid resistance is 41Ω) gradually increases in the first term and the second term in which the positive pulse group appears, and gradually decreases in the third term and the fourth term in which the negative pulse group appears. Since the body resistance Z includes a capacitive component, the capacitive component is charged in the second term in which the positive pulse group appears, and is discharged in the third term in which the negative pulse group appears. Also, the capacitive component is inversely charged in the fourth term in which the negative pulse group appears, and is discharged in the first term in which the positive pulse group appears.

In the first term, the pulse width gradually widens, and thus, the change in voltage of the stimulation signal (the slope of the graph) in the first term becomes gradually steeper, whereas in the second term, the pulse width gradually narrows, and thus, the change in voltage of the stimulation signal in the second term becomes gradually gentler. Also in the third term and the fourth term, in the third term, the pulse width gradually widens, and thus, the change in voltage of the stimulation signal in the third term becomes gradually steeper, whereas in the fourth term, the pulse width gradually narrows, and thus, the change in voltage of the stimulation signal in the fourth term becomes gradually gentler. As a result, the stimulation signal, which is distorted by the action of the body's capacitive properties, exhibits a waveform that is analogous to a sine wave.

Further, in the description above, the pulse width is changed over time in the second term in a manner that the change-over-time thereof is reverse of the change-over-time of the pulse width in the first term, and the pulse width is changed over time in the fourth term in a manner that the change-over-time thereof is reverse of the change-over-time of the pulse width in the third term. This is done so that the distorted stimulation signal becomes analogous to a sine wave. Further, the change-over-time of the pulse width in the first term is the same as the change-over-time of the pulse width of the second drive signal in the third term, and the change-over-time of the pulse width of the first drive signal in the second term is the same as the change-over-time of the pulse width of the second drive signal in the fourth term. This is also done so that the distorted stimulation signal becomes analogous to a sine wave.

Distortion of Pseudo-Sine Wave in Comparative Example

Considering the equivalent circuit illustrated in FIG. 2B, the resistance component of the intracellular fluid, which is arranged in series with the capacitive element (cell membrane), is influential during charging of the capacitive element. On the other hand, the combined resistance components of the intracellular fluid and the extracellular fluid are influential during discharging of the capacitive element. Stated differently, as regards the body's reactance characteristics, there is a difference between charging resistance and discharging resistance. This results in that charging of the capacitive element is relatively fast, whereas discharging is relatively slow.

This imbalance in charging/discharging of the capacitive element causes a phenomenon wherein the period of time with a constant voltage is prolonged in the vicinity of the peaks (the highest potential points or the lowest potential points) of the pseudo-sine wave, as indicated by the regions surrounded by ellipses in FIG. 12A. (In each ellipse shown in the graph of FIG. 12A, the horizontal straight line portion is relatively long.) As a result, in the comparative example, the waveform of the pseudo-sine wave (stimulation signal) is distorted within the ellipses shown in the graph of FIG. 12A, and the third-order harmonic (8.1 kHz) is relatively large, as illustrated in FIG. 12B. In order to provide a soft stimulation to the body, however, it is desirable to suppress distortions in the sine wave (i.e., desirable to make the waveform of the stimulation signal analogous to a sine wave), and desirable to suppress the third-order harmonic.

It should be noted that, although the regions surrounded by the ellipses in FIG. 12A are for the graph for when the intracellular fluid resistance is 1Ω, the same phenomenon occurs in cases where the intracellular fluid resistance is 41Ω (resistance close to that of a living body), wherein the period of time with a constant voltage is prolonged in the vicinity of the peaks (the highest potential points or the lowest potential points) of the pseudo-sine wave. Also, as illustrated in FIG. 12B, the third-order harmonic (8.1 kHz) is relatively large also in cases where the intracellular fluid resistance is 41Ω (resistance close to that of a living body).

So, in the present embodiment, discharge pulses are generated in order to promote discharging, which tends to be relatively delayed. The discharge pulses are described below.

Discharge Pulses of the Present Embodiment

Figure 3:
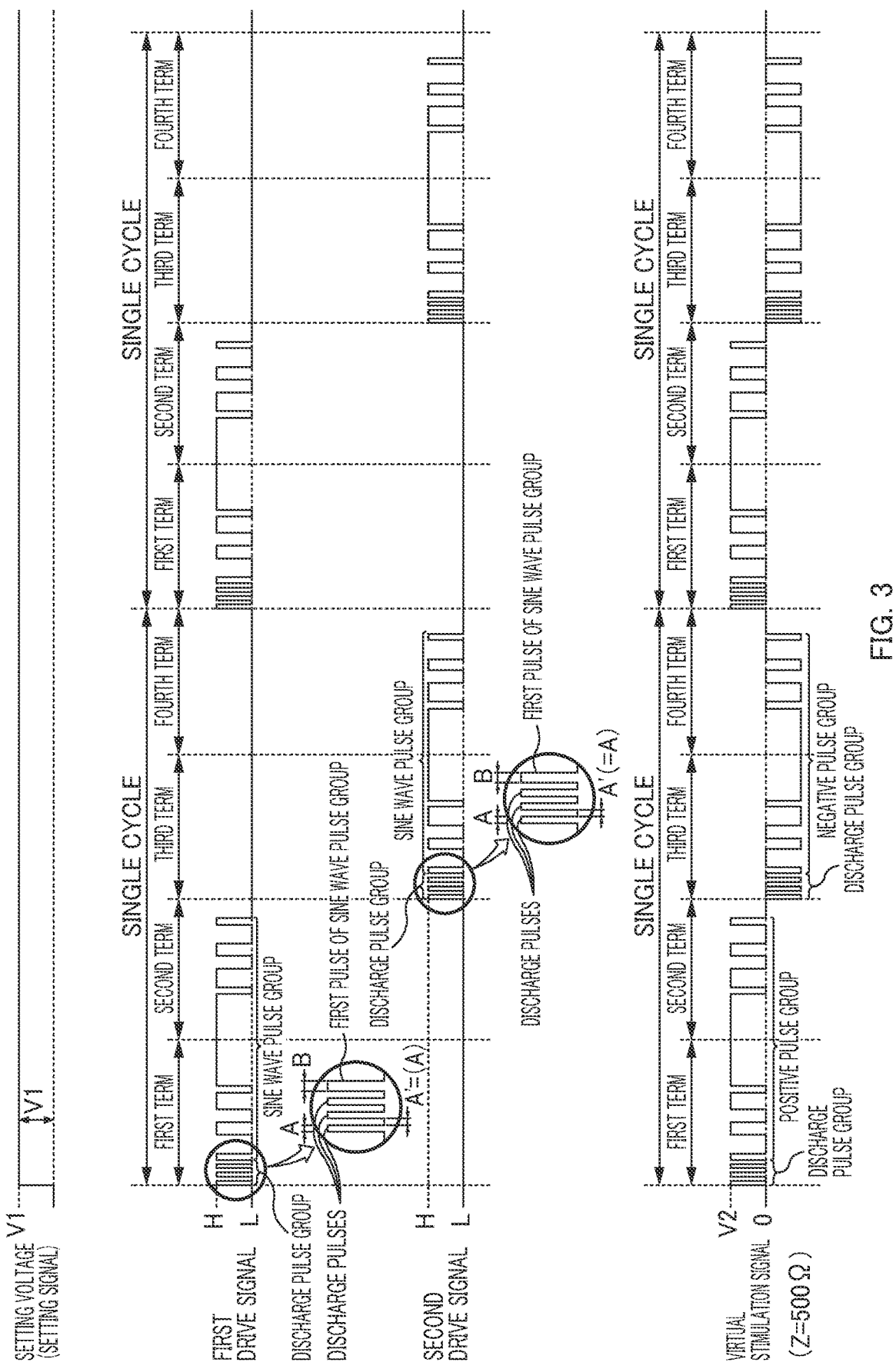
FIG. 3 is a diagram illustrating various types of signals according to a first embodiment.

FIG. 3 is a diagram illustrating various types of signals according to the first embodiment. In the figure, the horizontal axis indicates time, and the vertical axis indicates voltage. The various types of signals illustrated in the figure are, in order from above, the setting voltage, the first drive signal, the second drive signal, and a virtual stimulation signal.

The first drive signal of the present embodiment includes sine wave pulse groups and discharge pulses. The second drive signal also includes sine wave pulse groups and discharge pulses. The first drive signal and the second drive signal are shifted from one another by 180 degrees in phase.

The sine wave pulse group of the first drive signal is the same as the pulse group in the first drive signal of the comparative example. Thus, in the first term (the former half of the energization term of the first drive signal), the pulse width of the plurality of pulses constituting the sine wave pulse group of the first drive signal gradually widens (the duty cycle gradually increases), and in the second term (the latter half of the energization term of the first drive signal), the pulse width gradually narrows (the duty cycle gradually decreases). Further, the pulse width in the second term changes over time in a manner that the change-over-time thereof is reverse of the change-over-time of the pulse width in the first term. Thus, when focusing on the sine wave pulse group (excluding the discharge pulses) on the graph of the first drive signal in the figure, the waveform of the pulse group in the first term and the pulse group in the second term has line symmetry with respect to the borderline between the first term and the second term.

The sine wave pulse group of the second drive signal is the same as the pulse group in the second drive signal of the comparative example. Thus, in the third term (the former half of the energization term of the second drive signal), the pulse width of the plurality of pulses constituting the sine wave pulse group of the second drive signal gradually widens, and in the fourth term (the latter half of the energization term of the second drive signal), the pulse width gradually narrows. Further, the pulse width in the fourth term changes over time in a manner that the change-over-time thereof is reverse of the change-over-time of the pulse width in the third term. Thus, when focusing on the sine wave pulse group (excluding the discharge pulses) on the graph of the second drive signal in the figure, the waveform of the pulse group in the third term and the pulse group in the fourth term has line symmetry with respect to the borderline between the first term and the second term. The change-over-time of the pulse width of the second drive signal in the third term is the same as the change-over-time of the pulse width of the first drive signal in the first term. The change-over-time of the pulse width of the second drive signal in the fourth term is the same as the change-over-time of the pulse width of the first drive signal in the second term.

The discharge pulses of the first drive signal and the second drive signal are pulses immediately before the first pulse of the sine wave pulse group, and are pulses for promoting discharging of electric charge accumulated in the body's capacitive component. The discharge pulses of the first drive signal are pulses generated in the first term, and serve as pulses for discharging electric charge that has been charged in the capacitive component in the fourth term. The discharge pulses of the second drive signal are pulses generated in the third term, and serve as pulses for discharging electric charge that has been charged in the capacitive component in the second term. It should be noted that the discharge pulses of the first drive signal are signals for generating positive discharge pulses in the stimulation signal, and the discharge pulses of the second drive signal are signals for generating negative discharge pulses in the stimulation signal. When focusing on the entire pulse group including the sine wave pulse group and the discharge pulses on the graph of the first drive signal in the figure, the waveform of the pulse group in the first term and the pulse group in the second term is asymmetric, because the discharge pulses are formed only in the first term. Similarly, when focusing on the entire pulse group including the sine wave pulse group and the discharge pulses on the graph of the second drive signal in the figure, the waveform of the pulse group in the fourth term and the pulse group in the fifth term is asymmetric, because the discharge pulses are formed only in the third term.

When the pulse width of the discharge pulse of the first drive signal (and the second drive signal) is defined as A and the pulse width of the first pulse in the sine wave pulse group is defined as B, the pulse width A of the discharge pulse is set to less than or equal to the pulse width B of the first pulse in the sine wave pulse group (A≤B). In this example, the pulse width A of the discharge pulse (and the halt width A' of the discharge pulse) is 2 µs, whereas the pulse width B of the first pulse in the sine wave pulse group is set to 3 µs. The shorter the pulse width, the less stimulation the body feels. (High-frequency pulses are less likely to cause stimulation to a living body compared to low-frequency pulses.) Thus, by setting the pulse width A to less than or equal to the pulse width B, it is possible to suppress stimulation to the body caused by the discharge pulses.

In the present embodiment, the first drive signal (and the second drive signal) includes a plurality of discharge pulses. In cases where the pulse width of the discharge pulses is short, a single discharge pulse can only achieve a small discharge amount. However, by generating a plurality of discharge pulses, discharging of redundant charge can be promoted. In the first embodiment, the discharge pulse group of the first drive signal is constituted by three discharge pulses, but the number of discharge pulses is not limited thereto. Further, as described further below, the number of discharge pulses may be changed depending on various conditions.

In the present embodiment, the frequency of the discharge pulse group (the plurality of discharge pulses) of the first drive signal (and the second drive signal) is set higher than the frequency (PWM frequency; for example, the frequency of the triangular wave signal of FIG. 11) of the sine wave pulse group. In this way, stimulation to a living body caused by the discharge pulse group can be suppressed.

The virtual stimulation signal illustrated in FIG. 3 is a signal in a state where there is no distortion in waveform caused by the body's reactance characteristics. When a resistance (e.g., 500Ω) including no capacitive component nor inductive component is connected to the outputting units 31, a signal substantially matching the virtual stimulation signal will be outputted from the outputting units 31.

As in the comparative example, also in the virtual stimulation signal of the present embodiment, the positive pulse groups and the negative pulse groups for generating a pseudo-sine wave appear alternately at predetermined intervals, as illustrated in the figure. Further, in the present embodiment, plus-side discharge pulses (positive discharge pulses) are generated immediately before each positive pulse group, and minus-side discharge pulses (negative discharge pulses) are generated immediately before each negative pulse group. The positive discharge pulses are pulses that are generated in the first term of the stimulation signal, and are for discharging electric charge that has been charged in the capacitive component by the negative pulse group in the fourth term. The negative discharge pulses are pulses that are generated in the third term of the stimulation signal, and are for discharging electric charge that has been charged in the capacitive component by the positive pulse group in the second term.

When the pulse width of the discharge pulse (positive discharge pulse or negative discharge pulse) of the stimulation signal is defined as A and the pulse width of the first pulse in the positive pulse group (or the negative pulse group) is defined as B, the pulse width A is set to less than or equal to the pulse width B (A≤B). In this example, the pulse width A (and the halt width A') is 2 μs, whereas the pulse width B is set to 3 μs. The shorter the pulse width, the less stimulation the body feels. (High-frequency pulses are less likely to cause stimulation to a living body compared to low-frequency pulses.) Thus, by setting the pulse width A to less than or equal to the pulse width B, it is possible to suppress stimulation to the body caused by the discharge pulses.

Figure 4A:
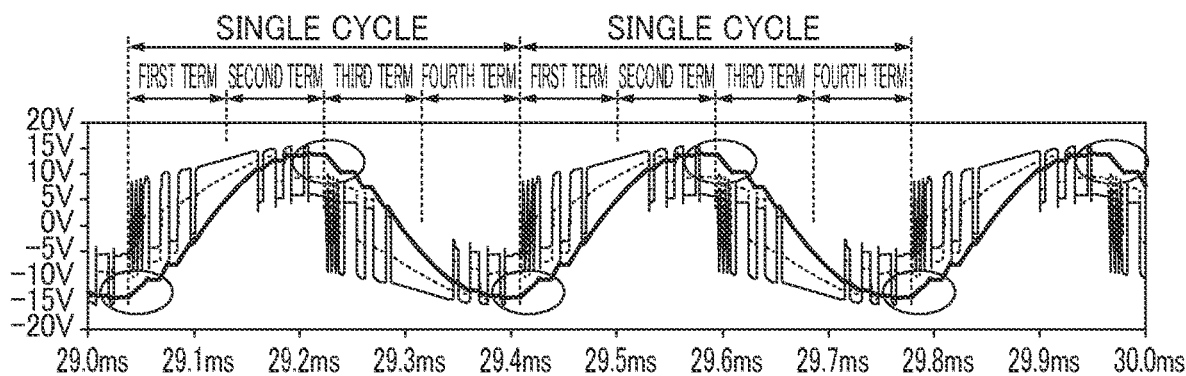
FIG. 4A is a graph for when a stimulation signal of the first embodiment is outputted from outputting units 31 in a state connected with body resistance Z.

FIG. 4A is a graph (simulation result) for when a stimulation signal of the first embodiment (cf. FIG. 3) is outputted from the outputting units 31 in a state connected with body resistance Z. The horizontal axis of the graph indicates time, and the vertical axis indicates voltage between the outputting units 31. Note that, as in the comparative example, the frequency is 2700 Hz (a single cycle is around 370 μs). Also, as in the comparative example, the capacitance of a cell membrane is 1 μF, and the extracellular fluid resistance is 2 kΩ. The thick solid line, the dotted line, and the thin solid line in the graph respectively indicate different intracellular fluid resistances, which are 1(Ω), 41(Ω), and 100(Ω), respectively.

Substantially similar to the comparative example, the stimulation signal, which is distorted by the action of the body's capacitive properties, exhibits a waveform that is analogous to a sine wave, as illustrated in FIG. 4A. Further, as indicated by the regions surrounded by the ellipses in the figure, in the present embodiment, the period of time with a constant voltage is shortened in the vicinity of the peaks (the highest potential points or the lowest potential points) of the pseudo-sine wave. This is because discharging is promoted by the application of the discharge pulses (positive discharge pulses and negative discharge pulses) of the stimulation signal in the first term and the third term. As a result, the waveform of the pseudo-sine wave is closer to a sine wave, and stimulation applied to a living body can be softened.

Figure 4B:
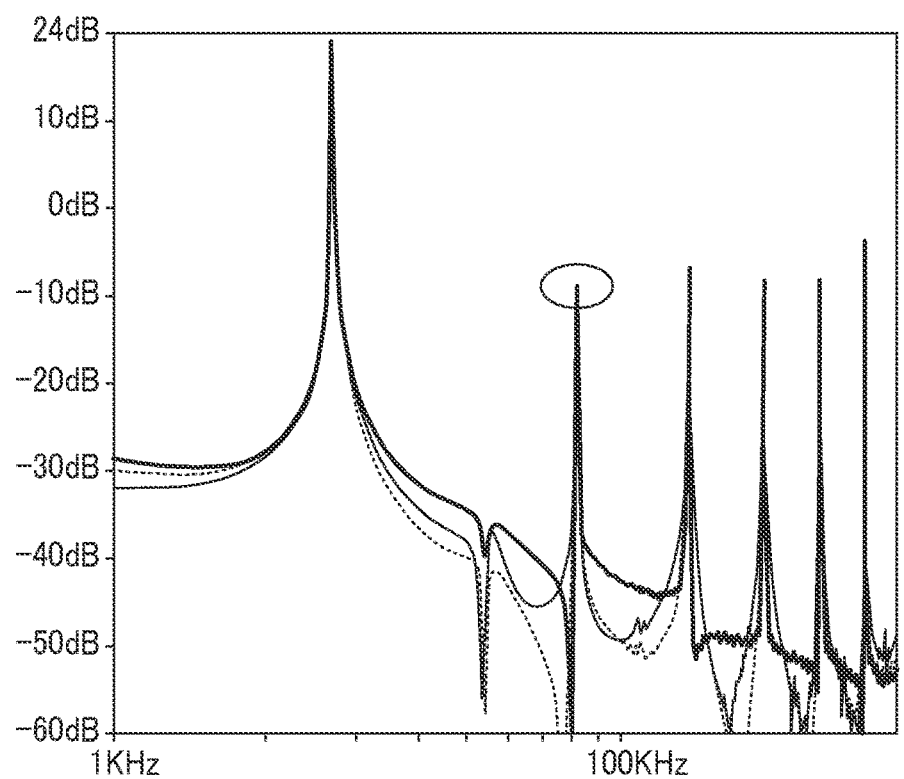
FIG. 4B is a graph illustrating a FFT analysis result of FIG. 4A.

FIG. 4B is a graph illustrating a FFT analysis result of FIG. 4A. In the present embodiment, the waveform of the pseudo-sine wave is closer to a sine wave compared to the comparative example, and as illustrated in FIG. 4B, the third-order harmonic (8.1 kHz) is reduced by about 6 dB (around one-fourth or less in electric power) compared to the comparative example. Also from this FFT analysis result, it can be verified that the discharge pulses of the present embodiment can suppress distortions in the waveform of the pseudo-sine wave (stimulation signal). Also from this FFT analysis result, it can be verified that the present embodiment softens stimulation applied to a living body.

Second Embodiment

If the same stimulation is continuously applied to a living body, the body gets used to the stimulation and becomes less likely to feel the stimulation. So, the frequency of the stimulation signal may be changed, in order to change the stimulation applied to the body.

Figure 5:
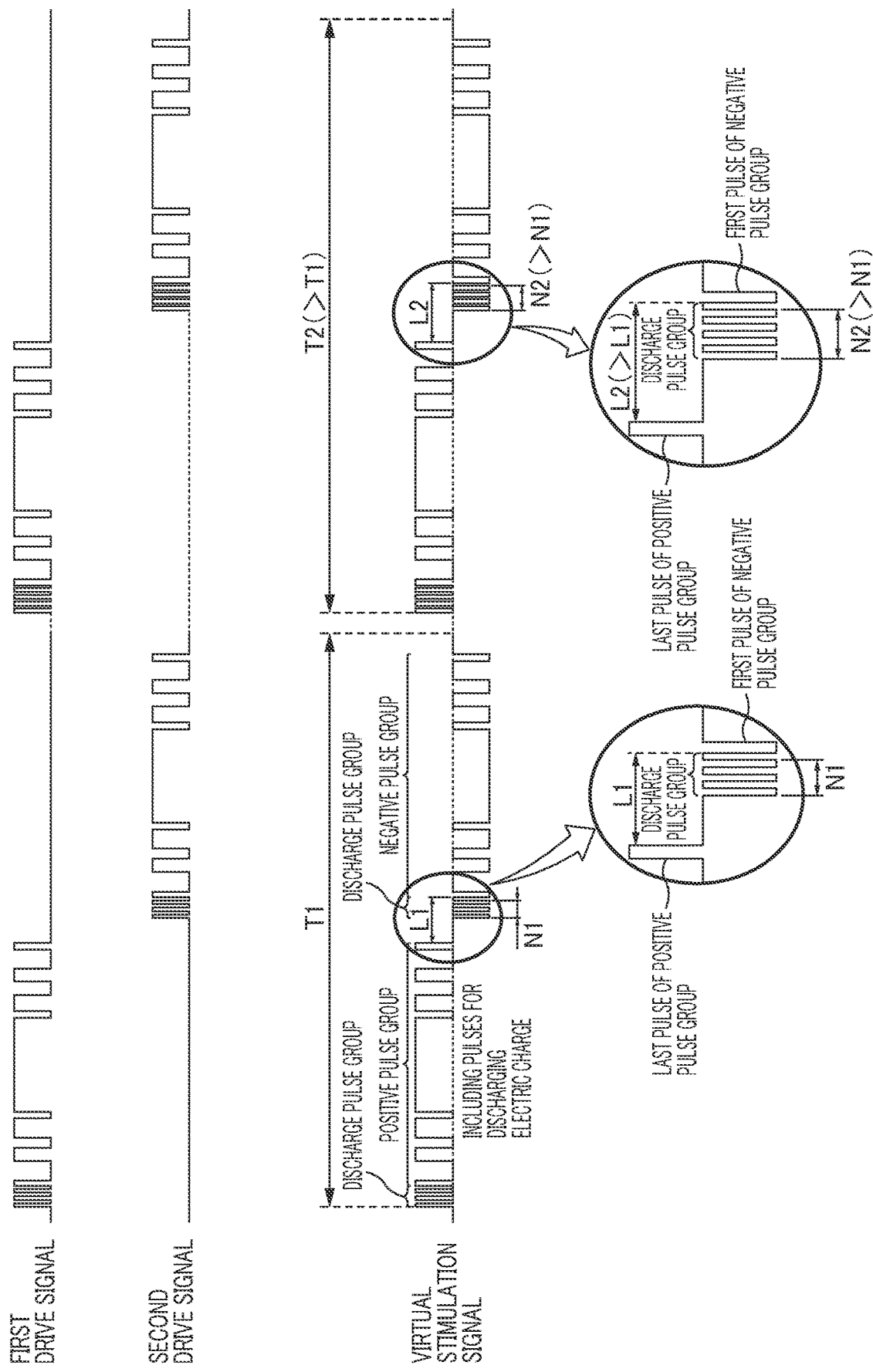
FIG. 5 is a diagram illustrating a virtual stimulation signal according to a second embodiment.

FIG. 5 is a diagram illustrating a virtual stimulation signal according to a second embodiment. The figure illustrates waveforms of the various signals worth a single cycle in a case where the frequency is changed. This example assumes a case where the frequency is decreased; the period T2 after the frequency change is longer than the period T1 before the frequency change.

In cases where the frequency is changed, the halt term between the positive pulse group and the negative pulse group in the virtual signal also changes. It should be noted that, in cases where the frequency of the virtual signal is changed without changing the waveform of the sine wave pulse groups of the first drive signal and the second drive signal, but by changing the period thereof, the halt term between the positive pulse group and the negative pulse group in the virtual signal also inevitably changes. In this example, the term L2 from the last pulse in the positive pulse group to the first pulse in the negative pulse group after the frequency change as illustrated in the figure is longer than the term L1 from the last pulse in the positive pulse group to the first pulse in the negative pulse group before the frequency change. Also, the term L2 from the last pulse in the negative pulse group to the first pulse in the positive pulse group after the frequency change as illustrated in the figure is longer than the term L1 from the last pulse in the negative pulse group to the first pulse in the positive pulse group before the frequency change.

As described above, in cases where no discharge pulse is inserted, a phenomenon occurs wherein the period of time with a constant voltage is prolonged in the vicinity of the peaks (the highest potential points or the lowest potential points) of the pseudo-sine wave, which results in distortions in the waveform of the pseudo-sine wave. The period of time with a constant voltage, which is at the peaks of the pseudo-sine wave, occurs during the halt term between the positive pulse group and the negative pulse group, and therefore, if the halt term between the positive pulse group and the negative pulse group is prolonged (i.e., if the frequency is lowered), distortion in the waveform of the pseudo-sine wave will become more significant.

So, in the second embodiment, the number of discharge pulses in each discharge pulse group is changed in cases where the frequency is changed, or in cases where the halt term between the positive pulse group and the negative pulse group is changed. In the example illustrated in FIG. 5, the number of discharge pulses in each discharge pulse group is increased from three to four, in cases where the frequency is lowered, or where the halt term between the positive pulse group and the negative pulse group is prolonged. Further, in cases where the frequency is lowered, or where the halt term between the positive pulse group and the negative pulse group is prolonged, the term of the discharge pulse group is extended from N1 to N2.

FIGS. 6A and 6B are graphs (simulation results) for when a 2500-Hz stimulation signal is outputted from the outputting units 31 in a state connected with body resistance Z. The horizontal axis of each graph indicates time, and the vertical axis indicates voltage between the outputting units 31. FIG. 6A is a graph for when a discharge pulse group is constituted by three discharge pulses, and FIG. 6B is a graph for when a discharge pulse group is constituted by four discharge pulses. The pulse width (A) of each discharge pulse is 2 μs, and the halt term (A') is 2 μs. When there are four discharge pulses, the period of time with a constant voltage in the vicinity of the peak (the highest potential point or the lowest potential point) of the pseudo-sine wave is shorter, compared to when there are three discharge pulses. Further, although not illustrated in the figure, from FFT analysis results of the stimulation signals shown respectively in FIGS. 6A and 6B, it was found that, when there were four discharge pulses, the third-order harmonic (8.1 kHz) was reduced by about 2 dB, compared to when there were three discharge pulses. It should be noted that, when the number of discharge pulses was increased to five (cf. FIG. 8A), the third-order harmonic (8.1 kHz) deteriorated. Thus, for a 2500-Hz stimulation signal, the optimal number of discharge pulses was four.

FIGS. 7A and 7B are graphs (simulation results) for when a 2700-Hz stimulation signal is outputted from the outputting units 31 in a state connected with body resistance Z. The horizontal axis of each graph indicates time, and the vertical axis indicates voltage between the outputting units 31. FIG. 7A is a graph for when a discharge pulse group is constituted by two discharge pulses, and FIG. 7B is a graph for when a discharge pulse group is constituted by three discharge pulses. The pulse width (A) of each discharge pulse is 2 µs, and the halt term (A') is 2 µs. Although not illustrated in the figure, from FFT analysis results of the stimulation signals shown respectively in FIGS. 7A and 7B, it was found that, when there were three discharge pulses, the third-order harmonic (8.1 kHz) was reduced by about 2 dB, compared to when there were two discharge pulses. It should be noted that, when the number of discharge pulses was increased to more than three, the third-order harmonic (8.1 kHz) deteriorated. Thus, for a 2700-Hz stimulation signal, the optimal number of discharge pulses was three.

As described above, the optimal number of discharge pulses was four for a 2500-Hz stimulation signal, whereas it was three for a 2700-Hz stimulation signal. As can be seen, it is effective to change the number of discharge pulses in each discharge pulse group in cases where the frequency is changed (or where the halt term between the positive pulse group and the negative pulse group is changed). More specifically, it is effective to increase the number of discharge pulses in each discharge pulse group (i.e., it is effective to prolong the term of the discharge pulse group) in cases where the frequency is lowered (or where the halt term between the positive pulse group and the negative pulse group is prolonged or the period is prolonged).

Third Embodiment

In an ideal sine wave voltage waveform, when the voltage drops immediately after reaching the highest potential point, the potential drops in a manner that the voltage change (slope) becomes gradually steeper. Likewise, in an ideal sine wave voltage waveform, after the lowest potential point, the potential rises in a manner that the voltage change (slope) becomes gradually steeper. Thus, even in cases of making the constant-voltage waveform (distorted waveform) at the peak (highest potential point or lowest potential point) of the pseudo-sine wave analogous to a sine wave by employing the discharge pulse group, it is desirable that the voltage change (slope) is made gradually steeper.

FIG. 8A is a diagram illustrating a virtual stimulation signal according to a reference example. In the stimulation signal of the reference example, the plurality of discharge pulses constituting each discharge pulse group are arranged at even intervals. Stated differently, in the stimulation signal of the reference example, the halt term between the discharge pulses is constant.

FIG. 8B is a diagram illustrating a third embodiment. In the stimulation signal of the third embodiment, there are at least three discharge pulses constituting each discharge pulse group, and there are at least two halt terms between the discharge pulses. In the third embodiment, the halt term between the discharge pulses of the discharge pulse group is set so as to gradually shorten. In this way, in the third embodiment, it is possible to further promote discharging in the latter half of the energization term of the discharge pulse group than in the former half.

FIGS. 9A and 9B are graphs (simulation results) for when the stimulation signal is outputted from the outputting units 31 in a state connected with body resistance Z. The horizontal axis of each graph indicates time, and the vertical axis indicates voltage between the outputting units 31. Each discharge pulse group is constituted by five discharge pulses, and the pulse width (A) of each discharge pulse is 2 µs. In FIG. 9A, the halt term between the discharge pulses is 2 µs and is constant. In contrast, in FIG. 9B, the halt term between the discharge pulses of each discharge pulse group is set so as to gradually decrease. As a result, in FIG. 9B, the voltage after the peak (highest potential point or the lowest potential point) of the pseudo-sine wave changes smoothly so as to become gradually steeper, compared to FIG. 9A. Stated differently, the waveform of the pseudo-sine wave in FIG. 9B is closer to a sine wave, and thus, stimulation applied to a living body can be softened.

It is considered that, the longer the constant-voltage period of time in the vicinity of the peak of the pseudo-sine wave is when no discharge pulse is inserted, the more significant the effect of the third embodiment will be. Thus, the halt term between the discharge pulses of the discharge pulse group may be gradually shortened in cases where the frequency is lowered (or where the halt term between the positive pulse group and the negative pulse group is prolonged). Stated differently, the setting may be switched between a setting in which the halt term between the discharge pulses of the discharge pulse group is kept constant and a setting in which the halt term is gradually shortened, depending on frequency.

Others:

The foregoing embodiments are for facilitating the understanding of the present invention and are not to be construed as limiting the present invention. The present invention can be modified and/or improved without departing from the gist thereof, and it goes without saying that the present invention encompasses equivalents thereof.

Output Transformer 10:

In the foregoing embodiments, the first switch 21 is connected to one-end side of the primary-side winding of the output transformer, the second switch 22 is connected to the other-end side of the primary-side winding of the output transformer 10, and a predetermined voltage V1 is applied to the center tap 13 of the output transformer 10. Thus, the primary-side winding does not need to be divided, and an inexpensive output transformer 10 can be used. Note, however, that the primary-side winding of the output transformer 10 may be divided in two.

In the foregoing embodiments, the stimulation signal is outputted from the outputting units 31 to a living body with the configuration illustrated in FIG. 1. Note, however, that the configuration is not limited thereto, so long as a stimulation signal as described in the foregoing embodiments can be outputted from the outputting units.

REFERENCE SIGNS LIST

1: Living body stimulation device;
10: Output transformer;
11: First input terminal;
12: Second input terminal;
13: Center tap;
14: First output terminal;

15: Second output terminal;
21: First switch;
22: Second switch;
31: Outputting unit (conductor element);
40: Control unit;
41: Processing device;
42: Voltage setting unit;
42A: D/A converter;
42B: Amplifier;
43: Drive signal generating unit;
Z: Human body resistance.

The invention claimed is:

1. A living body stimulation device comprising:
an outputting unit that outputs a stimulation signal to a living body, wherein
the stimulation signal is a signal in which a positive pulse group and a negative pulse group appear alternately at predetermined intervals, the positive pulse group being constituted by a plurality of pulses whose potential rises toward the plus-side, the negative pulse group being constituted by a plurality of pulses whose potential falls toward the minus-side,
when a single period of the stimulation signal is divided into four terms consisting of a first term, a second term, a third term, and a fourth term,
the positive pulse group appears in the first term and the second term, wherein, in the first term, the pulse width gradually widens, and in the second term, the pulse width gradually narrows in a manner that change-over-time thereof is reverse of the change-over-time of the pulse width in the first term, and
the negative pulse group appears in the third term and the fourth term, wherein, in the third term, the pulse width gradually widens, and in the fourth term, the pulse width gradually narrows in a manner that change-over-time thereof is reverse of the change-over-time of the pulse width in the third term,
the stimulation signal includes a discharge pulse group constituted by a plurality of:
a discharge pulse that is provided immediately before the positive pulse group and whose potential rises toward the plus-side; and
a discharge pulse that is provided immediately before the negative pulse group and whose potential falls toward the minus-side, and
a frequency of the plurality of discharge pulses constituting the discharge pulse group is higher than a frequency of the plurality of pulses constituting the positive pulse group or the negative pulse group.

2. A living body stimulation device comprising:
an outputting unit that outputs a stimulation signal to a living body, wherein
the stimulation signal is a signal in which a positive pulse group and a negative pulse group appear alternately at predetermined intervals, the positive pulse group being constituted by a plurality of pulses whose potential rises toward the plus-side, the negative pulse group being constituted by a plurality of pulses whose potential falls toward the minus-side,
when a single period of the stimulation signal is divided into four terms consisting of a first term, a second term, a third term, and a fourth term,
the positive pulse group appears in the first term and the second term, wherein, in the first term, the pulse width gradually widens, and in the second term, the pulse width gradually narrows in a manner that change-over-time thereof is reverse of the change-over-time of the pulse width in the first term, and
the negative pulse group appears in the third term and the fourth term, wherein, in the third term, the pulse width gradually widens, and in the fourth term, the pulse width gradually narrows in a manner that change-over-time thereof is reverse of the change-over-time of the pulse width in the third term,
the stimulation signal includes a discharge pulse group constituted by a plurality of:
a discharge pulse that is provided immediately before the positive pulse group and whose potential rises toward the plus-side; and
a discharge pulse that is provided immediately before the negative pulse group and whose potential falls toward the minus-side, and
the number of discharge pulses constituting the discharge pulse group is changeable depending on the frequency of the stimulation signal.

3. A living body stimulation device comprising:
an outputting unit that outputs a stimulation signal to a living body, wherein
the stimulation signal is a signal in which a positive pulse group and a negative pulse group appear alternately at predetermined intervals, the positive pulse group being constituted by a plurality of pulses whose potential rises toward the plus-side, the negative pulse group being constituted by a plurality of pulses whose potential falls toward the minus-side,
when a single period of the stimulation signal is divided into four terms consisting of a first term, a second term, a third term, and a fourth term,
the positive pulse group appears in the first term and the second term, wherein, in the first term, the pulse width gradually widens, and in the second term, the pulse width gradually narrows in a manner that change-over-time thereof is reverse of the change-over-time of the pulse width in the first term, and
the negative pulse group appears in the third term and the fourth term, wherein, in the third term, the pulse width gradually widens, and in the fourth term, the pulse width gradually narrows in a manner that change-over-time thereof is reverse of the change-over-time of the pulse width in the third term,
the stimulation signal includes a discharge pulse group constituted by a plurality of:
a discharge pulse that is provided immediately before the positive pulse group and whose potential rises toward the plus-side; and
a discharge pulse that is provided immediately before the negative pulse group and whose potential falls toward the minus-side, and
the number of discharge pulses constituting the discharge pulse group is changeable depending on a term between the positive pulse group and the negative pulse group during which no pulses are generated.

4. A living body stimulation device comprising:
an outputting unit that outputs a stimulation signal to a living body, wherein
the stimulation signal is a signal in which a positive pulse group and a negative pulse group appear alternately at predetermined intervals, the positive pulse group being constituted by a plurality of pulses whose potential rises toward the plus-side, the negative pulse group being constituted by a plurality of pulses whose potential falls toward the minus-side, when a single period of the stimulation signal is divided into four terms consisting of a first term, a second term, a third term, and a fourth term, the positive pulse group appears in the first term and the second term, wherein, in the first term, the pulse width gradually widens, and in the second term, the pulse width gradually narrows in a manner that change-over-time thereof is reverse of the change-over-time of the pulse width in the first term, and the negative pulse group appears in the third term and the fourth term, wherein, in the third term, the pulse width gradually widens, and in the fourth term, the pulse width gradually narrows in a manner that change-over-time thereof is reverse of the change-over-time of the pulse width in the third term, the stimulation signal includes a discharge pulse group constituted by a plurality of:

a discharge pulse that is provided immediately before the positive pulse group and whose potential rises toward the plus-side; and a discharge pulse that is provided immediately before the negative pulse group and whose potential falls toward the minus-side, the discharge pulse group is constituted by at least three said discharge pulses, and a term between the discharge pulses is set so as to gradually shorten during which no pulses are generated.

5. The living body stimulation device according to claim 1, wherein, when the pulse width of the discharge pulse is defined as A and the pulse width of a first pulse in the positive pulse group or the negative pulse group is defined as B, A is set to be less than or equal to B.

6. The living body stimulation device according to claim 2, wherein, when the pulse width of the discharge pulse is defined as A and the pulse width of a first pulse in the positive pulse group or the negative pulse group is defined as B, A is set to be less than or equal to B.

7. The living body stimulation device according to claim 3, wherein, when the pulse width of the discharge pulse is defined as A and the pulse width of a first pulse in the positive pulse group or the negative pulse group is defined as B, A is set to be less than or equal to B.

8. The living body stimulation device according to claim 4, wherein, when the pulse width of the discharge pulse is defined as A and the pulse width of a first pulse in the positive pulse group or the negative pulse group is defined as B, A is set to be less than or equal to B.

* * * * *